United States Patent [19]

Chable et al.

[11] 4,350,168

[45] Sep. 21, 1982

[54] HYPERTHERMIC TREATMENT DEVICE

[75] Inventors: Yves A. Chable; Serge Lacroix; Philippe M. Rault, all of Dinan, France

[73] Assignee: Societe Anonyme de Telecommunications, France

[21] Appl. No.: 162,245

[22] Filed: Jun. 23, 1980

[30] Foreign Application Priority Data

Feb. 8, 1980 [FR] France ................... 80 02752

[51] Int. Cl.³ .............................................. A61B 5/00
[52] U.S. Cl. ................... 128/736; 128/798; 128/804
[58] Field of Search ............... 128/783, 798, 802, 803, 128/804, 420 A, 422, 736

[56] References Cited

U.S. PATENT DOCUMENTS

| 1,989,282 | 1/1935 | Kimble et al. | 12/798 |
| 3,817,252 | 6/1974 | Maurer | 128/798 |
| 3,895,639 | 7/1975 | Rodler | 128/422 |
| 4,016,886 | 4/1977 | Doss et al. | 128/804 X |
| 4,095,602 | 6/1978 | LeVeen | 128/804 X |
| 4,121,592 | 10/1978 | Whalley | 128/804 X |
| 4,196,737 | 4/1980 | Bevilacque | 128/798 |
| 4,237,898 | 12/1980 | Whalley | 128/804 X |
| 4,253,469 | 3/1981 | Aslan | 128/736 |

FOREIGN PATENT DOCUMENTS

| 662033 | 12/1935 | Fed. Rep. of Germany | 128/804 |
| 1109280 | 6/1961 | Fed. Rep. of Germany | 128/420 A |
| 2815156 | 10/1978 | Fed. Rep. of Germany | 128/804 |
| 371553 | 1/1907 | France | 128/798 |

Primary Examiner—Lee S. Cohen
Attorney, Agent, or Firm—Jacobs & Jacobs

[57] ABSTRACT

A device for hyperthermia treatment using radio-frequency generation applied externally to the surface of a patient's body and a temperature measuring device comprising thermocouples in hypodermic needles to be inserted in the patient's body, the output of each thermocouple being passed through a low-pass or band-stop filter to a switching device for selecting a given thermocouple and comparing its output to a reference thermocouple, and the output of the switching device being passed through a low-pass filter to a recorder.

2 Claims, 10 Drawing Figures

HYPERTHERMIC TREATMENT DEVICE

The present invention relates to a device for the medical treatment of certain human diseases, such as cancers.

More particularly, it relates to a device for the local or regional treatment of cancers, particularly localized deep rooted cancers, by overheating the tumoral mass, without affecting the healthy surrounding tissue.

Such hyperthermic treatment is achieved in known manner, by the action of a power generator at radio frequency, for example at 13.56 MHz, which power is applied by means of applicators or electrodes to the zones of the patient's body to be treated whilst monitoring the temperature of said zone. This zone includes the tumoral mass whose temperature it is desired to raise to a maximum in order to effect necrosis of said mass, and the healthy surrounding tissue whose temperature must not exceed 43° C.

The various temperatures at different points of the treated zone result from three factors; the electrical power applied, the nature of the tissues and the blood irrigation in said tissues. The influence of these factors makes it possible to attain a dynamic equilibrium governed by simple laws:

- the most heated points are also the most cooled if blood irrigation is sufficient,
- the healthy tissues are well heated and their temperature is regulated below lethal temperature, by the flow of blood,
- the bones and adipose tissues receive little power, but are likely to be overheated as they are poorly irrigated in their mass,
- the cancerous tumors receive a great deal of power as they are well hydrated and, being poorly irrigated, they are rapidly overheated, in hottest points being located at the centre of the tumors.

Device for carrying out such a hyperthermic treatment are already known, particularly by the article "Tumor Eradication in the Rabbit by Radiofrequency Heating" published by J. A. Dickson, S. A. Shab, Dr. Waggott and W. B. Whalley in "Cancer Research" Vol. 37, July 1977, pp. 2162–2169. However, the device described in this article is not adapted for the treatment of human beings, particularly because it uses rigid applicators for applying the electrical voltage to the patient's body, which incurs the risk of bruising the patient if they are applied with strong pressure, or of burning if they are not applied perfectly on the patient's skin.

The prior art also includes a device for hyperthermic treatment known under registered trademark "Magnetrode". This device, manufactured and distributed by Hyperthermia Division of Henry Electronics, Inc. preferably uses the magnetic field created by a solenoid or a toroid surrounding the zone to be treated or placed in the vicinity of the surface to be treated.

All these known devices, as well as the device according to the invention, use a radiofrequency generator at 13.56 MHz, but the device according to the invention distinguishes from the known devices by the nature of its applicators, by the particular system for measuring the temperatures in the zone subjected to the treatment and by the particular way in which the tuning of the power generator is achieved in accordance with the actual load impedance.

To this end, the device according to the invention comprises a power generator at radio frequency, at least two applicators for applying power to the patient's body, means for measuring temperatures at a plurality of points in the treated zone, wherein the applicators are supple and deformable, absorb humidity, are electroconductive, electrically connected to the power outputs of said generator and in good electrical contact with the patient's skin.

According to one embodiment, said applicators substantially comprise a supple, electroconductive fabric of which one of the faces or active surface, impregnated with an electroconductive gel, is in direct contact with the patient's skin, the other face of said fabric being in contact with the first face of a conductive metal knit to the other face of which, on the one hand, each strand of a supple multistrand conductor sheathed with an insulating plastic material in its part not in contact with said knit, is welded individually and in a substantially uniform distribution and, on the other hand, a sheet of resilient foam material of medium density is applied itself coated with a supple protective layer on which are applied, in part, one or more resilient adhesive tapes of which the other parts adhere to the patient's skin.

According to a modified embodiment of the present invention, said sheet of resilient foam material may be replaced by an inflatable bag. In this case, the inflatable bag which provides the pressure necessary for applying the supple conductive fabric on the patient's skin, is itself surrounded by moisture-absorbent compresses.

Still according to the present invention, said applicators have an active surface which is that of the supple conductive fabric, adapted to the zone to be treated, the supple conductive metal knit of smaller surface is centered on said supple conductive fabric and the foam sheet, of surface at least equal to the supple conductive fabric, covers all the conductive fabric and the conductive metal knit.

The device according to the invention for therapeutic treatment by hyperthermia which comprises, inter alia, means for measuring temperatures at a plurality of points in the treated zone, said means substantially comprising n thermocouples each placed inside a hypodermic needle, is also characterized in that there is inserted on each of the two leads of each thermocouple a low-pass of band-stop filter as near as possible to the output of said thermocouple in the patient's body, the output of each of these filters is connected to the input of a switching and temperature comparison device and in that the output of this comparison and switching devie is connected through a low-pass filter to the input of a recorder with vibrator and A.C. amplifier.

Still according to the present invention, the switching and temperatures comparison device substantially comprises a switch and a plate of $2(n+1)$ isothermal points of connection, each point of connection being connected, on the one hand, respectively to one of the 2 leads of the n thermocouples or to one of the 2 leads of a reference thermocouple and, on the other hand, for the first $2n+1$ points of connection, to the input terminals of the rotary switch and, for the point of connection $2n+2$ directly to the second output terminal of the switching and comparison device whose first output terminal is connected to the output terminal of the switch.

Still according to the invention, said reference thermocouple is a thermocouple of the same nature as the measuring thermocouples and it is permanently placed in a thermostatic bath composed of a mixture of distilled water and pure crushed ice whose temperature is monitored by one or more precision thermometers.

The device according to the invention is further characterized in that it comprises, in the intermediate vicinity of the applicators, a tuning circuit enabling the direct power delivered by said generator to be adapted in accordance with the arrangement of the power applicators so as to obtain a substantially zero reflected power.

Still according to the invention, said device comprises at least two applicators of which one is connected to an A.C. potential and the other to a zero potential, or both to an A.C. potential.

In a modification of the device according to the invention comprising three applicators, one is connected to an A.C. potential and the other two to a zero potential, or vice-versa.

In another modification of the device according to the invention, the applicators connected to an A.C. potential will advantageously comprise a central conductive zone connected to said A.C. potential, an insulating zone surrounding said central zone and an outer conductive zone connected, or not, to a potential and surrounding said insulating zone.

According to another modification of the present invention, the power generator comprises p power tubes supplying p outputs phase-shifted by $2\pi/p$ connected to at least 2 p power applicators.

According to this latter modification, said 2 p applicators will advantageously be placed on the patient's body so that the p electric fields thus created all contain the zone to be treated.

In all embodiments of the present invention, the voltage distributed on the applicators is caused not to comprise D.C. components, due to double safety means. By way of example, two capacitors, one of 100 pF and the other of 220 pF, are placed in series on the output circuit of the power generator.

The main advantage of the therapeutic device according to the invention lies in the supple nature of its applicators which, furthermore, are perfect electrical conductors, this allowing a direct electrical contact with the patient's skin and thus avoiding any risk of burning the patient.

Another advantage of the therapeutic device according to the invention resides in the possibility of choosing the number, shape and dimensions of the applicators, for each particular case.

Another advantage of the therapeutic device according to the invention resides in the high precision of the device for measuring the temperatures at various points of the treated zone, during treatment, said temperature measuring device being rendered, according to the invention, immune to the field of the radiofrequency waves emitted by the power generator and by all the electrical circuit which is connected thereto.

Another advantage of the therapeutic device according to the invention resides in the possibility of adjustable tuning of the load impedance of the power generator; this adjustable tuning results in a better use of the power emitted and a reduction in the interfering field created.

The invention will be more readily understood on reading the following description with reference to the accompanying drawings, in which.

Figure 4:
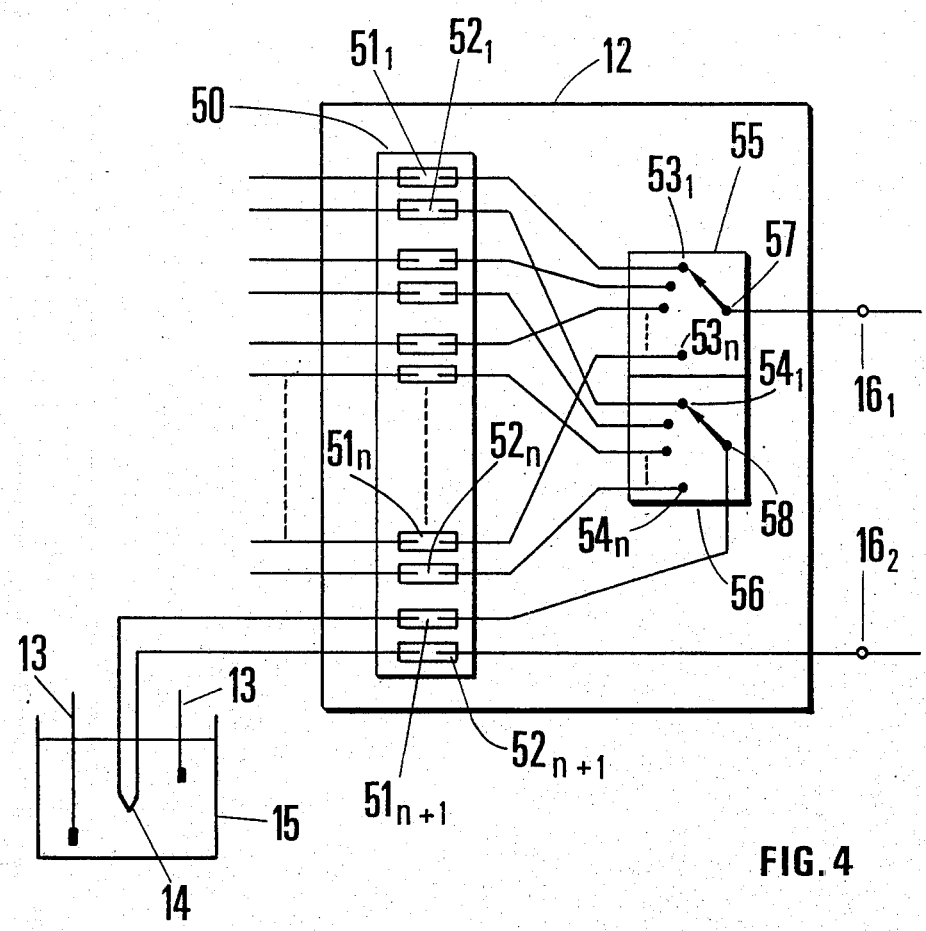

FIG. 4 schematically shows the switching and temperature comparison device.

Figure 5:
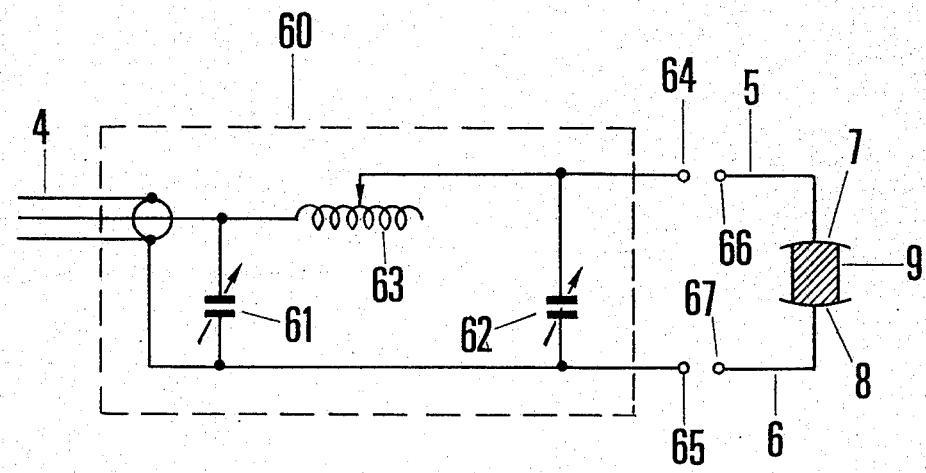

FIG. 5 shows the electrical diagram of the tuning device.

Figure 6:
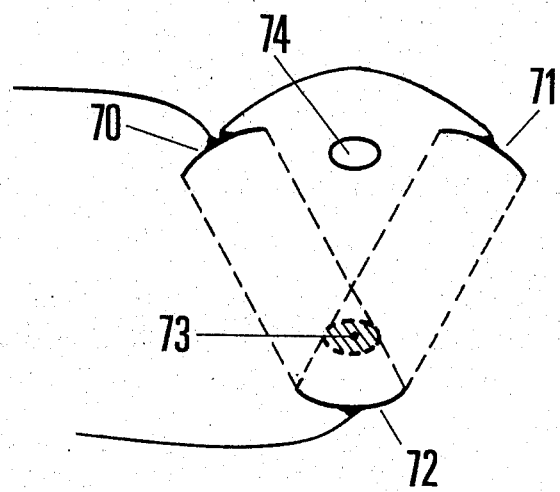

FIG. 6 shows an example of positioning of three applicators.

Figure 7A:
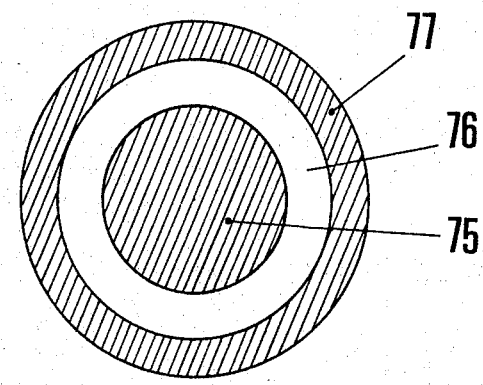
Figure 7B:
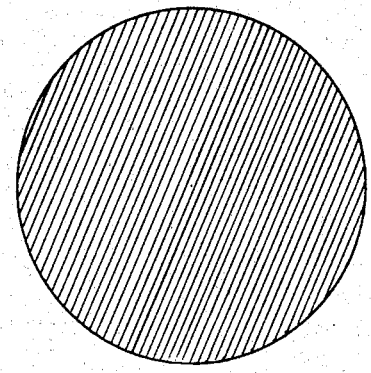

FIG. 7a and FIG. 7b show an embodiment of two applicators.

Figure 8:
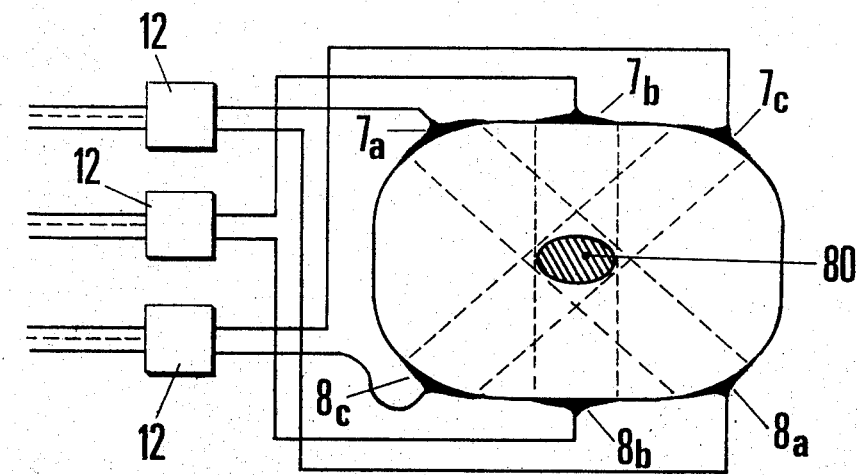

FIG. 8 shows an example of use of a device according to the invention using a generator with three phase-shifted outputs.

Figure 9:
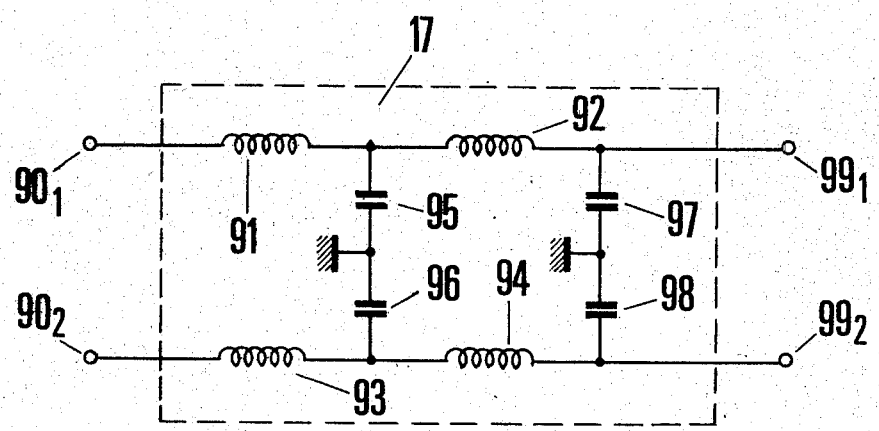

FIG. 9 shows the electrical diagram of the filter used at the input of the temperature recorder.

Figure 1:
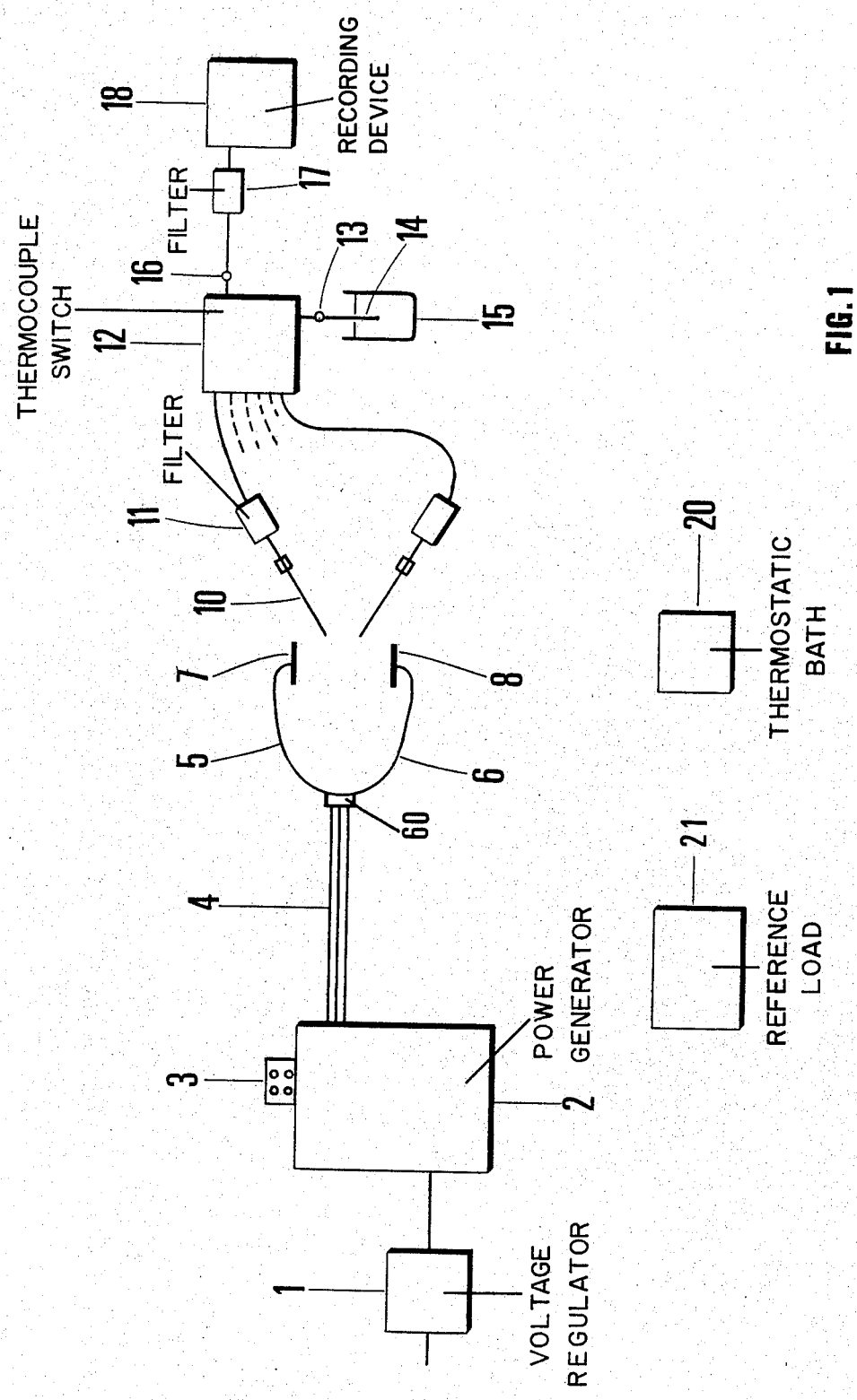
FIG. 1 is an overall schematic view of the therapeutic device according to the invention.

Referring now to the drawings, the device according to the invention shown in FIG. 1 comprises a voltage regulator 1, a power generator 2 and its instrument panel 3, a power output line 4 which terminates at 5 and 6 by the two supply leads of the supple applicators 7 and 8.

The device according to the invention also comprises the temperature measuring line which substantially comprises n thermocouples such as 10, and n filters such as 11, all connected to a thermocouple switch 12 comprising n+1 pairs of input terminals of which the (n+1)th pair is connected to a so-called reference thermocouple 14 immersed in a reference bath 15. The output terminal 16 of said thermocouple switch 12 is connected to the input of a filter 17 whose output is connected to the input of a recording device 18.

A thermostatic bath 20 and a reference load 21, for example of 50 Ω, are not really part of the device according to the invention, but are necessary for the suitable use thereof. Before the therapeutic device according to the invention is used, the thermostatic bath 20 serves to calibrate the thermocouples such as 10, and the reference load 21 serves to pre-adjust the power generator 2 and to verify it is functioning correctly.

Figure 2:
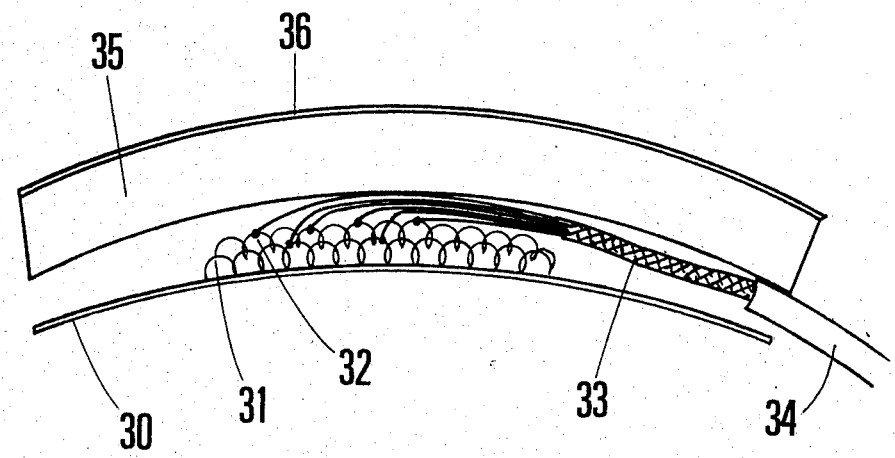
FIG. 2 shows a view in section of one of the applicators according to the invention.

FIG. 2 shows a section in transverse section through the applicators of the invention. This figure shows, at 30, a supple conductive fabric; at 31, a conductive metal knit on which are individually welded, for example at 32, the strands of a flexible conductor 33 insulated, in its part outside the applicator itself, by a plastic coating 34.

The unit thus formed is coated with a sheet 35 of elastic foam material of medium density, itself coated with a supple coating 36, placed on the top face of said sheet 35.

This coating 36, which is smooth on its top part, enables said applicator to be easily fixed to the patient's body by mean of medical adhesive tape.

By way of non-limitative example, the supple conductive fabric is a fabric usually used for making clothing for competing fencers. This fabric is then cut to be exact shape desired for the applicator. It is then coated with a conductive gel of such a type as used for making electrocardiograms and applied firmly at the desired spot. One, two or three thicknesses of metal knit are then placed on this supple conductive fabric; on the meshes of which knit the strands of the supply lead are individually welded. Still by way of example, said lead is a THT 15 KV cable of the non anti-parasite cable type formerly used for supplying automobile plugs.

With reference to FIG. 1, the thermocouple such as 10 are of the chromel-alumel type. Very fine chromel-alumel leads are found on the market which is already placed in a sheath of stainless steel filled with magnesia powder; it then suffices to carefully effect the welding of said thermocouple and to slide it in a catheter or hypodermic needle whose outer diameter is of the order of 0.6 to 1 mm, with the result that said thermocouple weld is slightly projecting from said catheter. A radiograph of the thermocouples enables the correct positioning of the whole to be checked so as to be sure that the thermocouple measures the temperature at the end of the probe and not the temperature inside the hypodermic needle.

Figure 3:
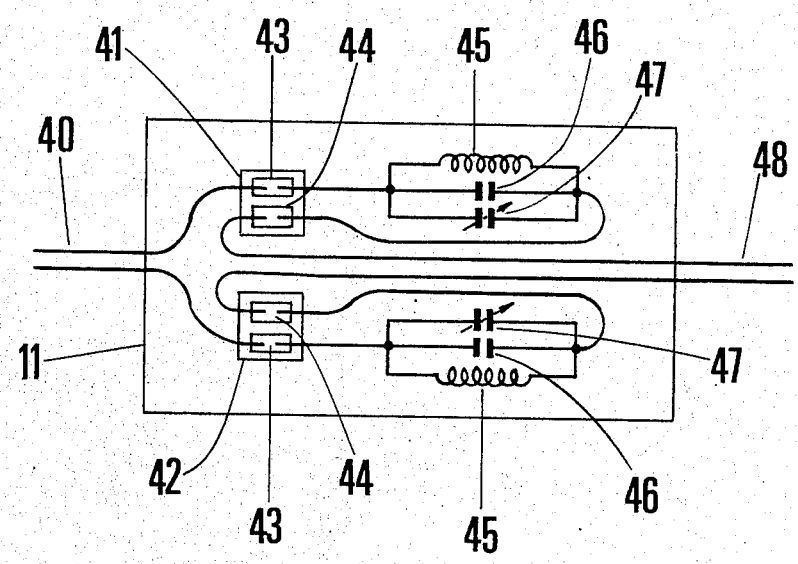
FIG. 3 shows an embodiment of the filter placed on each thermocouple lead near the patient's body.

Immediately at the outlet of the hypodermic needle, the chromel-alumel leads are interrupted by a filter, such as 11, of which one embodiment has been shown in detail in FIG. 3.

This Figure shows that the two leads of the thermocouple 40 arrive respectively on the contacts 41 and 42. Each of these contacts comprises an input connector 43 and an output connector 44 which are isothermal; to this end, they are mounted on a plate of beryllium oxide which is a good heat conductor whilst being an electrical insulator. Between these two connectors is inserted the filter proper which, here, by way of example, is an interference eliminator composed of a coil 45, a fixed capacitor 46 and a variable capacitor 47, connected in parallel. By way of example, the coil 45 is a silver coil of a value of 2 $\mu$H, the capacitor 46 is a ceramic capacitor of 68 pF and the capacitor 47 is an adjustable capacitor from 1 to 30 pF; all the connections between the input connectors 43 and output connectors 44 are silver wires and at the output of the output connector 44, chromel-alumel wires 48 are again used.

FIG. 4 shows the switch 12 making it possible on the one hand to select the thermocouple 10 of which it is desired to record the variations in temperature and, on the other hand, to connect said thermocouple to the reference thermocouple 14.

This switch 12 comprises an isothermal plate 50 on which are fixed n+1 pairs, $51_1$ and $52_1$ to $51_{n+1}$ and $52_{n+1}$ of connection contacts. By way of example, the isothermal plate is made of copper and the connection contacts are made of ceramics. Said connection contacts receive at one of their ends of the 2 n chromel-alumel leads of the n temperature measuring thermocouples such as 10 and the two leads of the reference thermocouple 14. The outputs of the connection contacts $51_1$ and $51_n$ inclusive are respectively connected to the different input contacts $53_1$ to $53_n$ of a first switch 55 coupled with a second switch 56 whose input contacts $54_1$ to $54_n$ are respectively connected to the outputs of the connection contacts $52_1$ to $52_n$. The output terminal 58 of the switch 56 is connected to the output terminal of the connection contact $51_{n+1}$, whilst the output terminal of the connection contact $52_{n+1}$ is connected to the output terminal $16_2$ of the device 12, the output terminal $16_1$ of said device 12 being connected to the output terminal 57 of the first switch 55.

The reference thermocouple 14 is immersed in a bath 15 of distilled water and pure crushed ice thermostatted at 0° C. and whose temperature is monitored by means of reference thermometers 13.

FIG. 5 shows the electrical diagram of the device for tuning the power emitted by the generator according to the impedance of the load which is included between the applicators. This tuning device 60 is placed between the generator and the applicators, as near as possible to the patient so that the distance from said device to the applicators is as short as possible. By way of non-limitative example in FIG. 5, two capacitors 61 and 62 adjustable from 30 to 300 pF and a coil 63 adjustable from 0 to 1 $\mu$H are used for making this filter, the two capacitors are mounted in parallel between the central conductor and the outer conductor of the coaxial cable 4 coming from the power generator, and the coil is mounted in series with the central conductor. The two output terminals 64 and 65 of this tuning device 60 are adapted to be connected to the access terminals 66 and 67 of the very short leads 5 and 6 supplying the two applicators 7 and 8. According to the impedance of the load 9, the adjustment of the capacitors 61 and 62 and the adjustment of the coil 63 are effected so as to use the maximum power available; to this end, the direct power and the reflected power are measured with precision and adjustment is effected so that the reflected power is always less than 5% of the direct power. Due to this tuning device 60, all sorts of configurations of applicators may be used: different shapes, surfaces, distances, positions on the body and relative positions of said applicators which may be necessitated by the treatments and patients' anatomy, may then be used.

Thus according to the invention, the supple electrodes may be of varied shape and also varied in number. Thus, in FIG. 5, two applicators 7 and 8 are placed opposite each other, one 7, is taken to an A.C. potential and the other 8, connected to earth. In FIG. 6, three applicators are used, the two applicators 70 and 71 being connected to earth and the applicator 72 being at an AC potential. Thus a tumor located for example at 73 is heated, whilst a fragile, for example osseous zone located at 74 is not subjected to the hyperthermic treatment.

Good results have also been obtained using circular applicators, one of which, shown in FIG. 7a presents a central conductive zone 75 taken to an A.C. potential, an insulating zone 76 and a conductive zone 77 not connected to a potential source, which serves in some respect as a guard ring, and the other, shown in FIG. 7b, is entirely conductive and connected to earth.

It is also possible to use a power generator having p power tubes supplying p outputs phase-shifted with respect to one another by $\pi/p$.—with each of the p outputs are associated at least two applicators; FIG. 8 shows by way of example three pairs of applicators 7a–8a, 7b–8b and 7c–8c supplied by the three outputs, phase shifted by $\pi/3$, of a power generator; each of the outputs having a power tuning device 12. The arrangement of the applicators is then such that the tumor to be treated, located for example at 80, has the three electric fields passing therethrough.

With reference to FIG. 1, a filter 17 is noted to be placed at the input of the temperature recorder 18. By way of non-limitative example, FIG. 9 shows the electrical diagram of a filter 17 whose use allows a correct measurement and recording of the temperature without interrupting the operation of the power generator. The two input terminals $90_1$ and $90_2$ of said filter 17 are respectively connected to the output terminals $16_1$ and $16_2$ of the thermocouple switching device 12. Still by way of example, the coils 91, 92, 93 and 94 have a value of 47 $\mu$H and the capacitors 95, 96, 97 and 98 are ceramic capacitors of 56 nF. The output terminals $99_1$ et $99_2$ of said filter 17 are connected to the input terminals of the recorder 18.

The apparatus according to the invention is intended for treatment of localized cancers by hypertermia. This apparatus may also be used for treating other diseases, for example for genito-urinary infections resistant to antibiotics.

What is claimed is:

1. A device for measuring the temperature of a tumor in a patient'body during heating of the tumor by external application to the tumor of a radiofrequency power, which comprises n thermocouples for measuring the temperature at a point inside the patient's body, each said thermocouple having two output leads, n hypodermic needles, and each said thermocouple being placed inside one of said hypodermic needles with the leads exiting therefrom, n band-stop filters, each of the said two output leads of each said thermocouple being connected to one of said band-stop filters as near as possible to the exit of the leads from each said hypodermic needle, a switching and temperature comparison means for selecting a said thermocouple inside the patient's body and comparing its output to a reference thermocouple, the output of each said filter being connected to the input of said switching and temperature comparison means, a low-pass filter connected to the output of said switching and temperature comparison means for enabling correct measurement of the temperature of the tumor without interrupting the application of said radiofrequency power, and a recorder connected to the output of said low-pass filter for recording said temperature.

2. The device according to claim 1, wherein said switching and temperature comparison means has first and second output terminals and $2(n+1)$ input terminals and comprises a plate of $2(n+1)$ isothermal points of connection, a first switch operable to select one of said thermocouples of which the temperature is intended to be recorded, and a second switch operable to connect said one thermocouple to a reference thermocouple having two output terminals, each said switch having one output terminal and n input terminals, said isothermal points of connection being connected, at the input side, to said band-stop filters connected to said thermocouples and, for the two last points of connection, to the two output terminals of the reference thermocouple, respectively, and at the output side, for the first 2n points of connection, to the input terminals of said first and second switches, respectively, and, for point of connection $2n+1$, to the output terminal of said second switch, and, for point $2n+2$ of said plate directly to the second output terminal of said switching and temperature comparison means, and the output terminal of said first switch being connected directly to the first output terminal of said switching and temperature comparison means.

* * * * *